United States Patent [19]

Fitzpatrick

[11] Patent Number: 5,053,704

[45] Date of Patent: Oct. 1, 1991

[54] FLOW IMAGER FOR CONDUCTIVE MATERIALS

[75] Inventor: Gerald L. Fitzpatrick, Redmond, Wash.

[73] Assignee: PRi Instrumentation, Inc., Torrance, Calif.

[21] Appl. No.: 463,409

[22] Filed: Jan. 11, 1990

[51] Int. Cl.$^5$ .................... G01N 27/82; G01N 21/21; G02F 1/09

[52] U.S. Cl. ................................... 324/235; 324/213; 324/238; 356/237; 359/282

[58] Field of Search ............... 324/200, 228, 213, 214, 324/215, 216, 235, 238, 244 OP, 244, 260, 262, 501; 350/374, 375, 376, 377, 378; 250/225; 356/237

[56] References Cited

U.S. PATENT DOCUMENTS

4,355,278 10/1982 Burns et al. ........................ 324/501
4,625,167 11/1986 Fitzpatrick ......................... 324/238

Primary Examiner—Walter E. Snow
Attorney, Agent, or Firm—Blakely, Sokoloff, Taylor & Zafman

[57] ABSTRACT

A device for the direct visualization of surface and near surface cracks, voids, flows, discontinuities, etc. in a target material. A magnetic garnet epitaxial film is deposited on either side, or both sides, of a non-magnetic substrate. A reflective material is provided adjacent to the epitaxial film, and the substrate with its associated layers is placed over a sheet of current carrying material and this sheet is placed over the target material. A bias magnetic field is then applied to the substrate together with its epitaxial film. Polarized light is transmitted onto the substrate with its associated layers and is reflected through the epitaxial layer and back out of the substrate. The existing magnetization, within the epitaxial film, interacts with nearby magnetic fields associated with eddy currents flowing adjacent to flaws in the target material, such that the domain structure of the epitaxial film is altered. The altered domain structure induces a rotation of the plane of polarization of the incident projected light. When viewed through a polarizing material disposed on the top epitaxial layer, the rotation of the reflected light renders the magnetic field variations associated with the flaws directly visible. Accordingly, surface and near surface flows within a skin depth, or slightly greater, of the electromagnetic fields associated with the currents in the current carrying sheet, are optically detected when eddy currents flow in the target material.

23 Claims, 5 Drawing Sheets

FLOW IMAGER FOR CONDUCTIVE MATERIALS

BACKGROUND OF THE INVENTION

1. Field of the Invention

The present invention relates to the field of detecting flaws and discontinuities in materials, and more particularly, to the detection of flaws and discontinuities in materials using magneto-optic visualization and eddy current excitation.

2. Art Background

The present application is related to U.S. Pat. No. 4,755,752, issued July 5, 1988 and U.S. Pat. No. 4,625,167 issued Nov. 25, 1986.

In many scientific, engineering and manufacturing applications, near surface cracks, voids, discontinuities and flaws in electrically conducting materials must be detected in order to insure the structural integrity of a material. For example, the material integrity of components comprising many air and space vehicles is critical for their proper operation, especially with regard to high stress components such as turbine and fan blades, rocket engine systems, air frames, etc.

A number of techniques have been developed and utilized in order to detect cracks, flaws, or the like, in such materials. For example, magnetic particle methods have been employed which utilize static or "low" frequency (less than 100 Hz) magnetic having field components parallel to the surface of ferromagnetic alloys, which may be induced by currents paralleling these surfaces. The parallel surface currents in may be induced, either directly, by contact electrodes, or indirectly, using coils or other arrangements of carrying conductors surrounding or adjacent to target material, and low frequency excitation. Magnetic fields paralleling the surfaces of the target material are distorted by cracks or near surface flaws and these portions may be detected through the use of a magnetic powder deposited on the material. Various types of powders have been developed for the the of the sub-surface flaws. Each magnetic particle in these typically consists of a single magnetic domain (i.e. region of essentially uniform magnetization). magnetic powder is applied dry or in a wet to a target material where a crack or flaw is present, the magnetic particles tend to aggregate and form a bridge regions of field nonuniformities which are a with the flaw. By mixing various pigments, dyes, and the like, with the magnetic powder, the cracks or flaws are rendered visible.

Although the magnetic powder technique is widely employed, it is a dirty and time consuming method which requires the induction of large surface currents or large applied fields in the material under study. Magnetic particle methods are best suited for use with low frequencies and ferromagnetic alloys. The inertial properties of magnetic particles renders the magnetic powder techniques ineffective when high frequencies are used. Moreover, magnetic particles do not work on non-ferromagnetic materials such as aluminum and other alloys used in the aerospace industry.

Another method which has been utilized in order to detect flaws or cracks in non-ferromagnetic materials is the "eddy" current technique. Eddy current techniques typically utilize a time varying electromagnetic field which is applied to the target material being examined. Non-contact coils are used to excite eddy currents in the target material, such that these currents tend to flow around flaws and result in field distortions which allow the flaw to be detected in a number of well known ways. For example, circuit parameters characterizing the mutual interaction between the exciting coil and the responding target material may comprise the parameters of capacitance, inductance or reactance. However, eddy current techniques require a considerable amount of support equipment and most techniques do not result in a flaw image but rather produce data from which flaw information can be obtained only after appropriate analysis has been completed.

As will be described, the present invention provides a method for the direct visualization of surface and near surface cracks, flaws, etc. in non-ferromagnetic and ferromagnetic conducting materials. The present invention provides direct visualization of the dynamic magnetic fields associated with the various flaws or other discontinuities in a target material, and overcomes the disadvantages associated with prior art material flaw imaging methods. In addition, the present invention is compatible with the requirements of eddy current methods while producing images of flaws directly, without the additional support equipment and data analysis required by most eddy current systems.

SUMMARY OF THE INVENTION

A method for the direct visualization of surface and near surface cracks, voids, flaws, discontinuities, etc. in a material is disclosed. The detection of flaws or the like is accomplished by the visualization of the dynamic magnetic fields, associated with the flow of induced electric currents near various flaws in a conducting target material.

A magnetic garnet epitaxial film is deposited on either side, or both sides, of a non-magnetic substrate. In one embodiment, a reflective coating or material is provided adjacent to the epitaxial film, and the substrate with its associated layers is placed over a sheet of current carrying material and this sheet is placed over the target material. A bias magnetic field is then applied to the substrate together with its epitaxial film. Polarized light is transmitted onto the substrate with its associated layers and is reflected through the epitaxial layer and back out of the substrate. The existing magnetization, within the epitaxial film, interacts with nearby magnetic fields associated with eddy currents flowing adjacent to flaws in the target material, such that the domain structure of the epitaxial film is altered. The altered domain structure induces a rotation of the plane of polarization of the incident projected light. When viewed through a polarizing material disposed on the top epitaxial layer, or at some distance away, through such a polarizing material, the rotation of the reflected light renders the magnetic field variations associated with the flaws directly visible. Accordingly, surface and near surface flaws within a skin depth, or slightly greater, of the electromagnetic fields associated with the currents in the current carrying sheet, are optically detected when eddy currents flow in the target material.

DETAILED DESCRIPTION OF THE INVENTION

A method for magneto-optically visualizing fatigue cracks, inclusions, voids, discontinuities, etc. (hereinafter collectively referred to as "flaws") in non-ferromagnetic or ferromagnetic conducting materials is disclosed. In the following description, for purposes of explanation, numerous details are set forth such as specific garnet or magneto-optic materials, substrates, optical configurations, bias magnetic fields, coils, induced currents, frequencies, etc. in order to provide a thorough understanding of the present invention. However, it will be apparent to one skilled in the art that the invention may be practiced without these specific details. In other instances, well known optical components, structures and electrical processing means have not been described in detail in order not to obscure the present invention unnecessarily.

Figure 1:
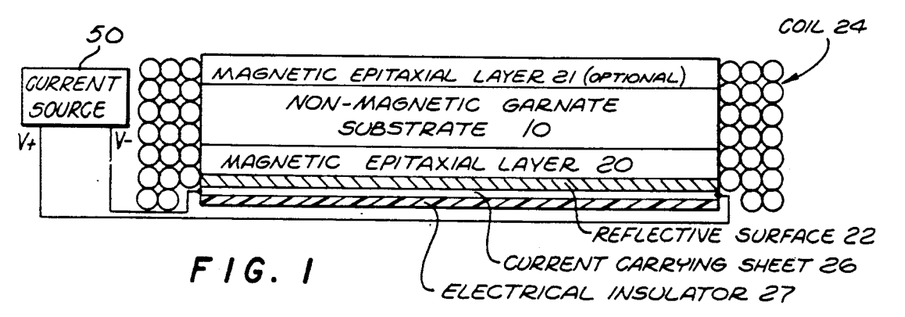
FIG. 1 illustrates an epitaxial garnet film and reflective coating disposed on a non-magnetic substrate disposed on a conducting sheet and an electrical insulator.

Referring now to FIG. 1, the presently preferred embodiment of the invention utilizes a non-magnetic garnet substrate 10 on which magnetic garnet epitaxial layer 20 and an optional layer 21 is disposed. As shown, a reflective surface 22 is provided using well known deposition techniques or materials on or just below the epitaxial layer 20, such that incident light passing through the substrate 10 and layers 20 and 21 is reflected back through layer 20, substrate 10 and layer 21, and flaws thereby imaged in a manner which will be discussed more fully below. It will be noted that the reflective surface 22 may comprise a front surface mirror or "Scotchlite" type coating (which is a retroreflective coating), as well as other numerous deposited or other reflective coatings. As shown in FIG. 1, a thin current carrying conducting sheet 26, which could have the reflective layer 22 provided on its surface if desired, is placed below the substrate with its epitaxial layers. Below the conducting sheet 26 is placed an electrical insulator 27. As will be discussed, the current carrying sheet 26 is provided with a potential difference, which results in oscillating electric currents in this sheet, which produces an electromagnetic field that in turn induces eddy currents in the target material. As shown in FIG. 1, an electrical coil 24 is disposed around substrate 10 with its associated layers. As will be discussed, coil 24 is provided with an electric potential in order to induce a current in the coil which produces a bias magnetic field in the magneto-optic material, namely in layers 20 and 21. This magnetic field "leaks through" and is also applied to the target material. However, the primary intent of the coil 24 is to apply a bias magnetic field to the magneto-optic material, which is layer 21 and 22. This bias field, when added to the weak magnetic fields from the distorted eddy currents in the target material, serves to produce an image of the flaws located in the target material in the magnet-optic layers 20 and 21. It should be noted that the current carrying sheet 26 is thin relative to a skin depth corresponding to the frequency of the electric current in this sheet. This allows the weak magnetic fields from the distorted eddy currents, due to flaws in the target material, to penetrate the conducting sheet 26 and the magneto-optic layers 20 and 21. For purposes of this Specification, the term "epitaxial layer" or "epitaxial garnet layer" or "epitaxial garnet film" or "garnet film", or "garnet film detectors" or "magneto-optic material" is understood to mean any one of a variety of suitable magneto-optically active film types having magneto-optic activity as required by the present invention for any particular application.

Figure 2:
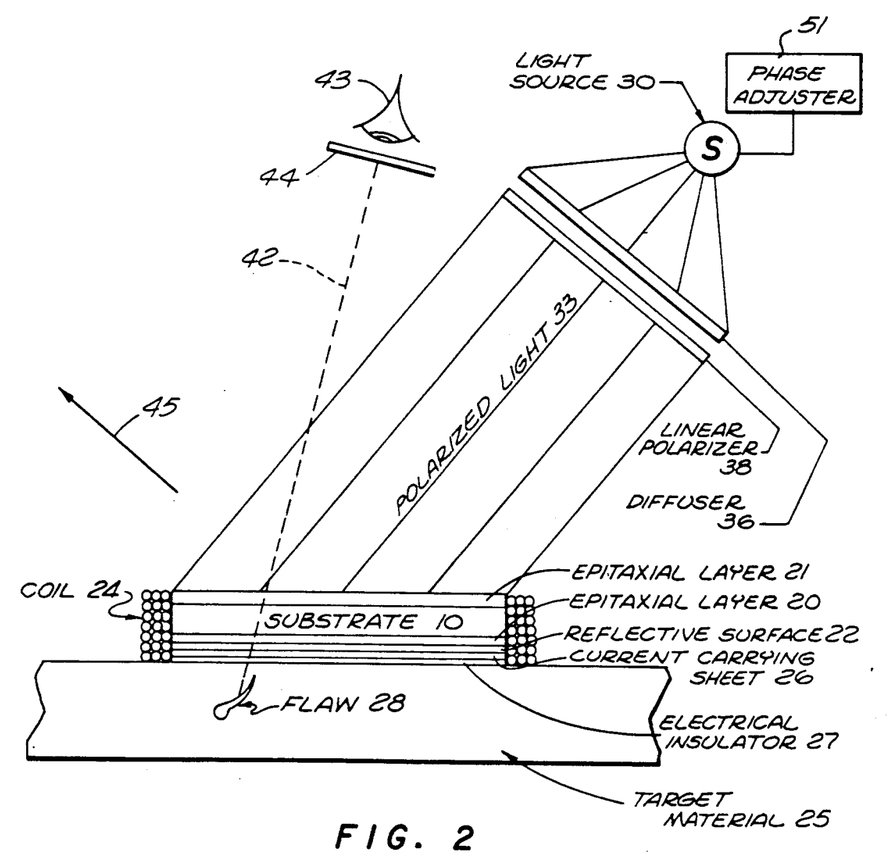
FIG. 2 illustrates one embodiment of the present invention utilizing a reflection geometry to optically detect flaws within a test material.

With reference now to FIG. 2, one embodiment of the present invention is disclosed which utilizes a reflection geometry. An electrically conducting target material 25 is provided which may include an unknown flaw 28 within the structure of the material 25. Substrate 10 with its magneto-optic layers 20 and 21 is disposed over a portion of the target material 25 to be examined. An electromagnetic field is applied to the test material 25 and substrate 10 with its applied layers 20, 21 by passing a current through the conducting sheet 26 or, alternatively, by attaching electrodes directly to the target material 25 or by other electromagnetic means. FIG. 1 shows in schematic form a current source 50 coupled directly to the current carrying sheet 26. A bias magnetic field is provided to layers 20 and 21 by passing a current (typically very low frequency) through the coil 24. A light source 30 which may comprise, for example, an incandescent bulb, single wave-length laser, fluorescent lamp, or the like, is provided in order to generate incident light 32. A diffuser 36 is provided to diffuse light rays 32 generated by light source 30. Similarly, a linear polarizer 38 is disposed adjacent to, and in optical alignment with, the diffuser 36 such that light generated by light source 30 is linearly polarized after passing through diffuser 36.

As shown in FIG. 2, the now polarized light 33 is projected onto the substrate 10 with associated layers disposed above the target material 25, and, as will be discussed more fully below, flaws 28 are rendered directly visible by observing the reflected radiation 42 reflected off of reflective surface 22 and passing through a second linear polarizer 44 to the eye or a camera 43.

When the polarized light 33 is incident on the garnet epitaxial layer 20, the plane of polarization of the incident light will be rotated by an angle $\theta f$ which may be described by the following relationship:

$$\theta \alpha \vec{f K} \cdot \vec{M}$$

Where $\theta f$ is the specific Faraday rotation of the layer 20, $\overline{K}$ is the wave vector of the incident light, and the $\overline{M}$ is the local magnetization of the epitaxial layer 20 at the point where the incident light passes through the layer. The sign of the scalar product $\overline{K}\cdot\overline{M}$ determines the sense of the rotation. It will be noted that in the case of a solid, the Faraday rotation does not depend on the sign of the wave vector $\overline{K}$, but only on the angle between $\overline{K}$ and $\overline{M}$. Thus, the effect of rotation is doubled by the reflective surface 22 disposed between the upper surface of the target material 25 and the magneto-optic layer 20. The reflective surface 22 ensures that the incident light 33 will pass back through the epitaxial layer 20 and thereby double the effective rotation of the plane of polarization. It will be appreciated that although not required, the presently preferred embodiments include a second epitaxial layer 21 disposed above substrate 10. This second layer 21 is generally separated from lower layer 20 by approximately 0.02 inches (the thickness of substrate 10 in the preferred embodiment), and has been found to increase the sensitivity of the present invention and improve contrast. However, for purposes of clarity, the analysis of the operation of the present invention disclosed hereinbelow will assume layer 21 is not present.

The difference in the rotation of the plane of polarization of the incident linearly polarized light 33 and the reflected light 42, which passes through the epitaxial layer 20, permits the direct visualization of flaws within target material 25. Ordinarily in the absence of an applied magnetic field, magnetic domains (regions of uniform magnetization in the epitaxial layer 20) are relatively small. In many epitaxial magnetic garnet films, especially those used in magnetic bubble memories or the like, domains typically measure several microns across. In other epitaxial films, small applied fields (of, for example, 100 Gauss or less) can cause the magnetic domains to coalesce into large domains several centimeters across in epitaxial film layers having comparable or larger diameters.

Figure 3:
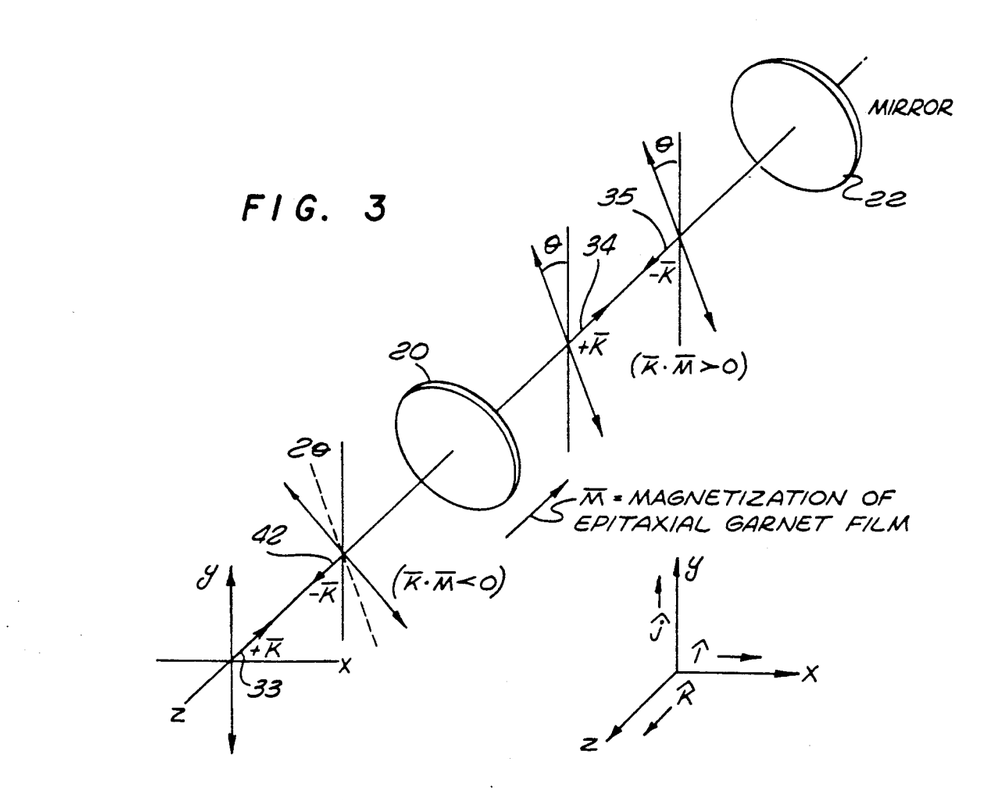
FIG. 3 illustrates the Faraday effect of a magneto-optically active garnet film on the plane of polarization of an incident light wave.

Referring now to FIG. 3, the effect of a magnetic garnet epitaxial layer 20 on the plane of polarization of incident linearly polarized light 33 is illustrated in more detail. A light wave which is one representative ray of the incident light 33 illustrated in FIG. 2 has a wave vector $+\overline{K}$ along the negative Z axis which is linearly polarized along the Y axis. As light wave 33 passes through a uniformly magnetized epitaxial layer 20 travelling toward reflective surface 22, the polarization of this light wave is rotated counterclockwise by an angle $\theta$ to become light wave 34 As light wave 34 impinges on reflective surface 22, the wave vector is reversed and light wave 35 passes back through the epitaxial layer 20 to become light wave 42. Thus, a doubled Faraday rotation of the polarization of light wave 33 occurs such that the plane of polarization of the light wave 42 is now $2\theta$ with reference to the Y axis or original polarization direction.

Figure 4A:
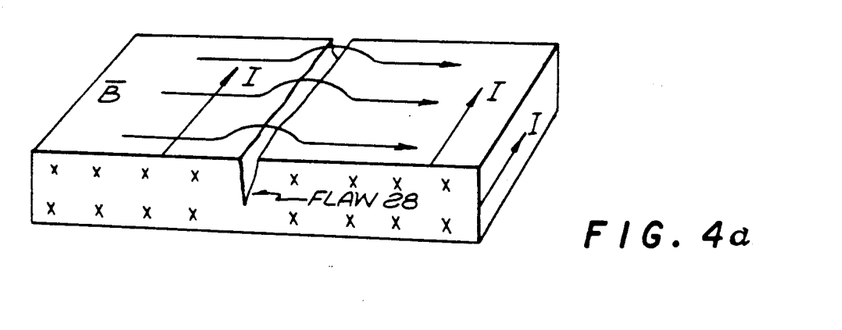
FIG. 4(a) illustrates magnetic fields induced by currents which fields effectively "jump" a flaw or other discontinuity in a ferromagnetic test material.
Figures 4B, 4C:
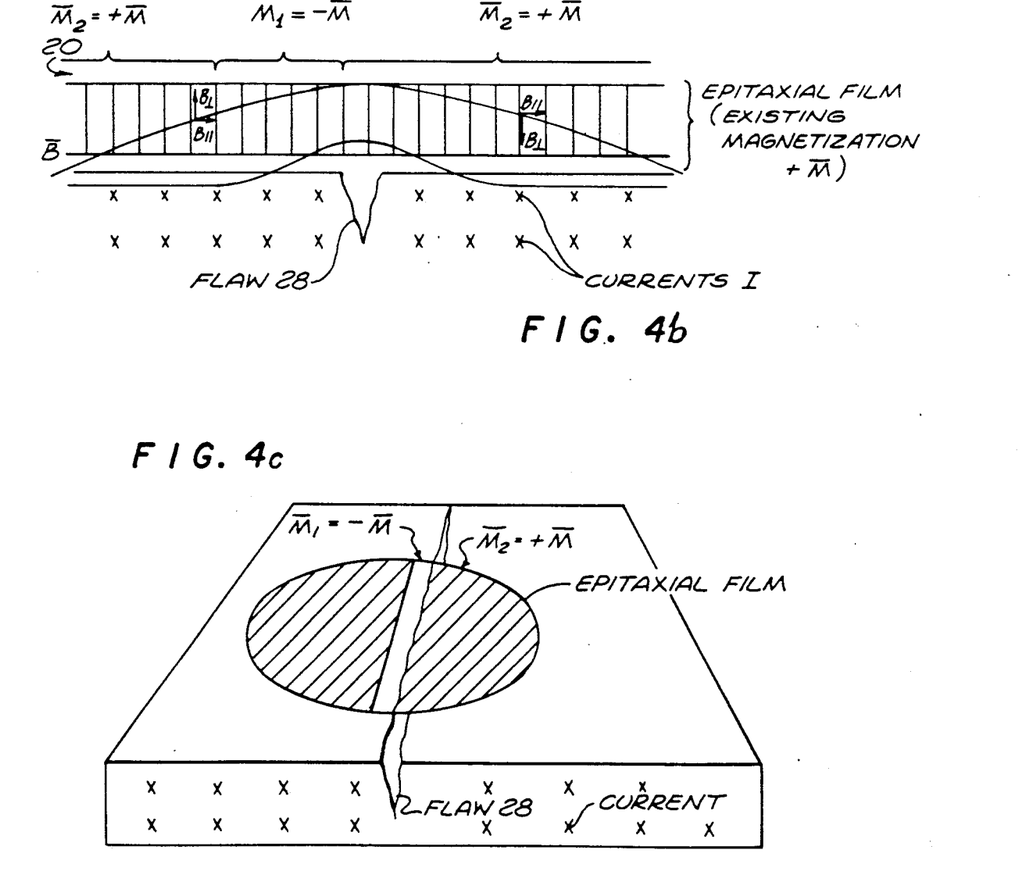
FIG. 4(b) illustrates the domain structure of the epitaxial layer in the presence of a magnetic field from a flaw in a ferromagnetic test material.
FIG. 4(c) illustrates an image, magneto-optically produced, of a flaw within a ferromagnetic test material using the teachings of the present invention.

Referring now to FIGS. 4(a)-(c), it be appreciated that the magnetic fields associated with eddy currents flowing near, and parallel to the long axis of a flaw in a ferromagnetic material, and produced by the conducting sheet 26 are capable, when combined with an appropriate bias magnetic field from coil 24, of switching the direction of existing magnetization at some point in the epitaxial layer 20 from $+\overline{M}$ to $-\overline{M}$. As shown in FIG. 4(a), a small flaw 28 has an associated magnetic field ("B field") distortion which will switch the magnetization of epitaxial layer 20 in regions parallel to the flaw [see FIG. 4(b)]. The plane of polarization of the light which passes through the region with magnetization $\overline{M}_1 = -\overline{M}$ is rotated by an angle $$\theta_1 \alpha \overline{K}_1 \cdot \overline{M}_1 > 0$$

but the plane of polarization of the light that passes through the adjacent region with magnetization $\overline{M}_2 = +\overline{M}$ is rotated by an angle $$\theta_2 \alpha \overline{K}_1 \cdot \overline{M}_2 < (|\theta_1| \simeq |\theta_2| \simeq \theta)$$

Thus, the total angle between the planes of polarization of the two light waves initially is zero, whereas after passing through the two adjacent regions having opposite magnetization it is:

$$2\theta \simeq |\theta_1| + |\theta_2|$$

As indicated in FIG. 3, the effect of reflective surface 22 is to double the angle of rotation of polarization, resulting in an angle of $4\theta$ between the planes of polarization of the two light waves upon passage back through the epitaxial layer 20. The light 42 which is returned to the viewer 43 is passed through a second linear polarizer 44 (referred to as an "analyzer"), and the flaw or other subsurface defect is thereby detected as a visual image. In practice, this is accomplished by setting the analyzer 44 to block one and pass the other of the two light waves, the planes of polarization of which are separated by an angle of $4\theta$ as previously described. Thus, two adjacent regions having reversed magnetization $\overline{M}_1$ and $\overline{M}_2$, in each of the two epitaxial layers 20 and 21, or in one layer 20, are seen as being dark (light) or light (dark) respectively, depending on the setting of the analyzer 44. In other words, the region of "reversed" magnetization adjacent to the flaw boundary is rendered visible as illustrated in FIG. 4(c).

Thus, the present invention images perturbations of the state of existing magnetization in a particular region of the epitaxial layer 20, by either leaving the magnitude and direction of the existing magnetization unchanged, or reversing (switching) the magnetization in the region of layer 20 above the flaw in material 25, altogether. These perturbations are then visually "imaged" by the returned polarized light 42 through the use of polarizing analyzer 44. The addition of optional layer 21 does not alter the operation of the present invention but rather further doubles the angle of rotation of the plane of polarization of the incident light 33. While this embodiment referred to flaw imaging in a ferromagnetic material, the magnetic state of the layer 20 and 21 can be viewed in essentially the same way, no matter what the cause of their magnetization. This will be described in more detail later for non-ferromagnetic materials.

Figure 5:
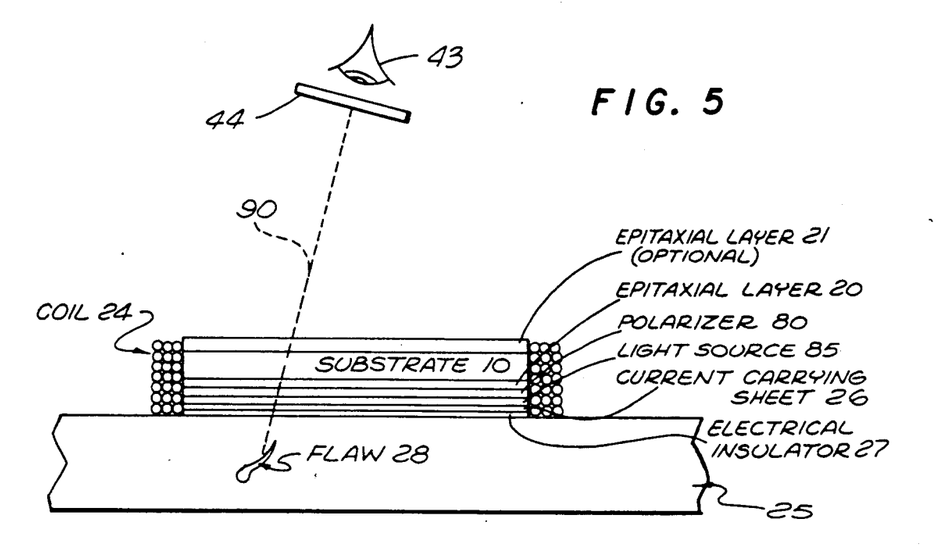
FIG. 5 illustrates another embodiment of the present invention utilizing a transmission geometry in order to optically detect flaws within a test material.

Referring briefly to FIG. 5, an alternate embodiment of the present invention is disclosed wherein a transmission geometry is utilized. As in the embodiment illustrated in FIG. 2, a non-magnetic substrate 10 is provided on which magnetic garnet epitaxial layer (or magneto-optic layer) 20 and optional epitaxial layer 21 are disposed. A linear polarizer 80 is sandwiched between the epitaxial layer 20 and diffuse light source 85, such as an electro-luminescent panel coupled to a voltage source. As shown, the substrate 10, magnetic epitaxial layers 20 and 21, polarizer 80, and the diffuse light source 85 are surrounded by coil 24. In addition an electrically conducting sheet 26 supplied with an oscillating electric current induces eddy currents in the conducting target material 25. These elements form an assembly which is placed in mechanical contact with target material 25 to be tested having a flaw 28. The diffuse light source 85 generates light which passes upwardly through polarizing layer 80, epitaxial layer 20, substrate 10, and through epitaxial layer 21. By viewing the light 90 passing through epitaxial layer 20, or through the epitaxial layers 20 and 21, through linear polarizer 44, magnetic field reversals and other magnetic field perturbations caused by flaw 28, as seen in epitaxial layer 20, may be directly viewed. Thus, the theory of operation of the embodiment disclosed in FIG. 5 is substantially the same as that described with reference to FIG. 2. Accordingly, just as in the case of FIG. 2, flaws are rendered visible in epitaxial layers 20 and optional layer 21 as a result of the rotation of the plane of polarization of incident light passing through layer 20 and optional layer 21.

It will be apparent to one skilled in the art, that if the magnetic fields associated with flaws are reversed, due to current reversals or the like [i.e. the currents in the conducting sheet 26 are alternating currents], these fields may be capable of switching the magnetization of the epitaxial layer 20 from $+\overline{M}$ to $-\overline{M}$ in some localized regions. In such an event, the pattern of light and dark as seen at 43 through the polarizing analyzer 44 is in synchrony with the current reversals. If such an alternating field is present, as is the case of the eddy current methods known in the prior art, it will be apparent that the image viewed at 43 through the analyzer 44 would tend to average to some uniform value and therefore "wash out". There are a number of methods which may be used in order to preserve the flaw image in the case of current reversals. One solution, discussed previously, is to add a small bias magnetic field to the garnet film 20 via current in the coil 24. Another solution is to amplitude modulate the illumination 33 of the garnet film 20 at the same frequency, and in some fixed phase relation, with the current reversals in 26. Similarly, it is possible to amplitude modulate the induced currents in the test material 25. Moreover, for very low frequency applications it is possible to "chop" the incident light wave 33 of FIG. 2 in synchrony with the electro-magnetic fields applied to 25. For higher frequency applications the incident light 33 could be amplitude modulated with various devices.

By amplitude modulating the incident light 33 in this, or some other manner, dark areas of a scene would always be viewed by a detector, or the eye at 43, through analyzer 44 as dark, and light areas of the scene would always appear light. Thus, the flaw 28 could be directly viewed at 43 even in the situation where the fields vary in time (e.g., the eddy current case). By adjusting the frequency of the electromagnetic field which excites the eddy currents, one can control the skin depth (the depth of penetration of the eddy currents), and therefore obtain information relative to the depth of the flaws detected by the present invention's method.

Figure 6:
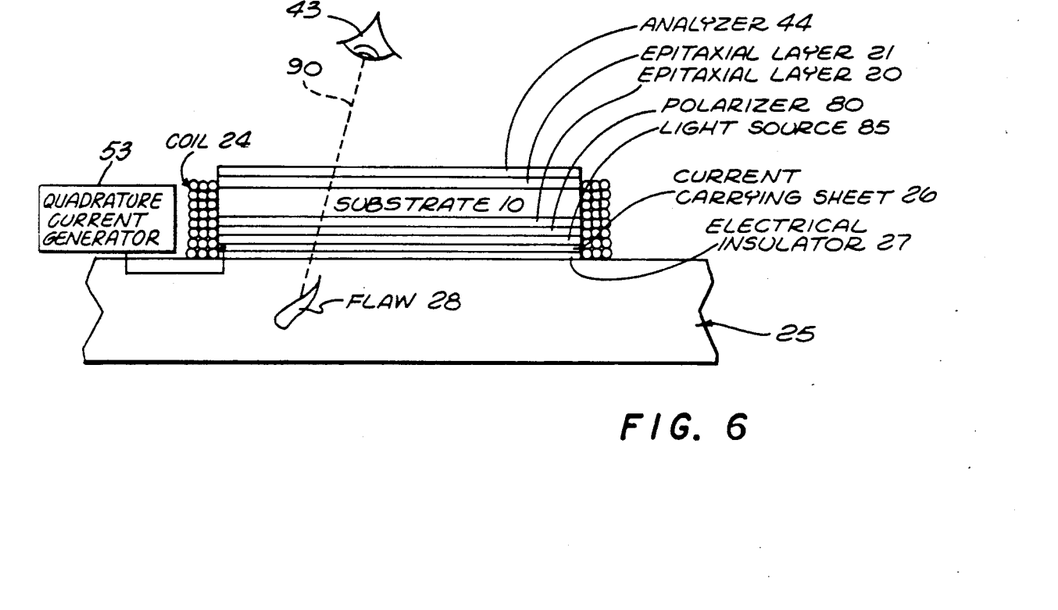
FIG. 6 illustrates an embodiment of the alternative present invention with the addition of an analyzer layer on the imaging device.

FIG. 6 illustrates an embodiment of the present invention utilizing a transmission geometry scheme as described in conjunction with FIG. 5. However, in this embodiment, an analyzer layer 44 is disposed on the surface of upper epitaxial layer 21. The layer 44 "analyzes" the light transmitted through the polarizer 80, the lower epitaxial layer 20, substrate 10 and upper epitaxial layer 21, enabling the distorted magnetic fields associated with the eddy currents in the target material 25 (produced by currents in the current carrying sheet 26) caused by flaws, such as flaw 28, to be directly viewed. By disposing the analyzer layer 44 directly on epitaxial layer 21, a more compact viewing device may be realized.

As with the embodiment illustrated in FIG. 5, the embodiment of FIG. 6 can be employed using only a single epitaxial layer 20 with upper epitaxial layer 21 eliminated. In this embodiment, analyzer layer 44 is disposed on the upper surface of substrate 10. Light from light source 85 is transmitted through polarizer 80, epitaxial layer 20 and substrate 10 through analyzer 44 to the viewer or camera 43. The use of a single epitaxial layer still allows magnetic field reversals and other perturbations to be observed, thus identifying flaw locations.

The present invention may be utilized for imaging flaws in non-ferromagnetic conducting materials. In non-ferromagnetic conducting materials (e.g. aluminum) where the magnetic permeability is low, low frequency applied magnetic fields are not appreciably distorted near flaws. In order to produce a sharp image of the flaw, it is necessary to produce a magnetic field which "jumps" over the flaw and stays near the flaw.

In order to maximize the imaging potential in non-ferromagnetic conducting materials, an electric current, which may be induced via the current carrying sheet 26 at a high frequency (e.g., 30 kHz), is injected into the target material 25. Such current injection results in a magnetic field (perpendicular to 25) having appreciable intensity only within a skin depth of the flaw as measured parallel to the surface of the target material 25 away from the flaw 28. This concentrated magnetic field area penetrates the thin conducting sheet 26 (26 is thin relative to the skin depth at the frequency of the current it carries) and the garnet film 20 and thereby defines the flaw. That is, an image of the magnetic fields in the garnet film 20 and 21 should resemble closely the flaw 28 in the target material 25. Although, in the preferred embodiment of the present invention, currents at eddy current frequencies in the range of 10 kHz to 100 kHz are typically utilized, any suitable current frequency which causes the magnetic field perpendicular to 25 to be appreciable within a skin depth from 28 as measured along, and parallel to the surface of 25, will suffice. In order to obtain useful (persistent) images in this method, a static or time varying bias magnetic field (provided by a current in coil 24) or other means such as as permanent magnet, must be applied to layer 20 and 21. This bias field, when added to the fields produced by the high frequency eddy currents (at a typical frequency of 10 kHz to 100 kHz) associated with a flaw 28, results in an image of the flaw seen in 20 and 21 that does not "wash out", but persists even though fields associated with the eddy currents are constantly reversing (at 10 kHz to 100 kHz in the preferred embodiment).

Figure 7:
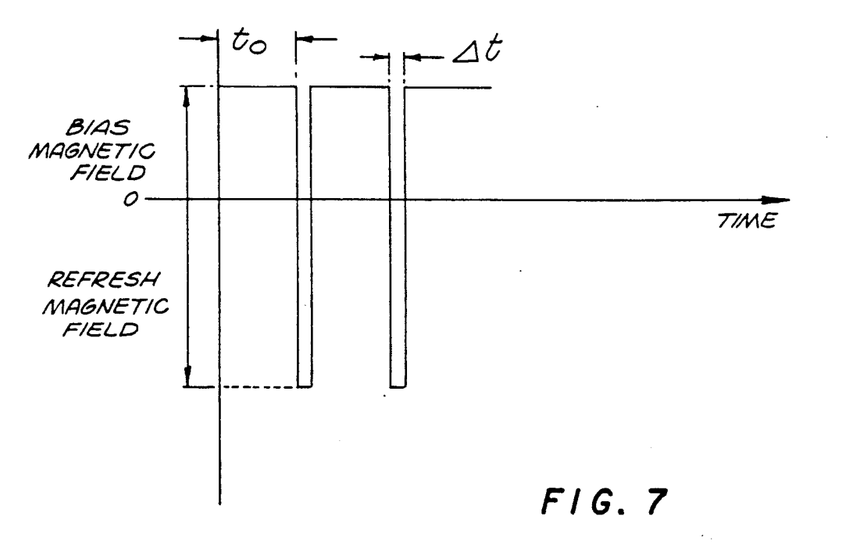
FIG. 7 diagrammatically illustrates how the applied bias and refresh magnetic fields in the present invention may be varied over time in order to provide a persistent image on the garnet film.

In one embodiment, the current in coil 24 is arranged to produce a bias and "refresh" magnetic field in opposite directions as shown in FIG. 7.

In this case the state of magnetization of the garnet film is "refreshed" (uniformly magnetized in one direction) during a short time interval $\Delta t$, and it is biased by a magnetic field in the opposite direction (these are arbitrary directions which, however, are both perpendicular to the plane of 25, 20 and 21) for a much larger period of time $t_o$. In this way an image of the flaw as soon in 20 and 21 is present for a large fraction $(1-\Delta t/t_o)$ of the time, and the garnet film is being erased or refreshed a small fraction $(\Delta t/t_o)$ of the time. The practical significance of this is that if one wishes to scan a target material rapidly by moving the assembly of FIG. 2 or 6, the resultant image seen on the garnet film 20 and 21 will tend not to smear, since the garnet film is constantly being erased and/or refreshed as shown in FIG. 7.

It will be appreciated by those skilled in the art that in any such embodiment, the garnet film must have a memory. That is, it must retain its state of magnetization after the refresh pulse has passed. Then, when the bias field is added to the fields from the flaws as already described, the garnet film can reverse this preexisting state of magnetization near the flaw, thereby making the flaw visible. Since the garnet film has a memory, such an image will be retained, even if the current in the sheet 26 is turned off.

It will be appreciated by those skilled in the art that other garnet films may exist that have no memories. These films would not remain in a state of uniform magnetization after a refresh pulse of the type described. Such films would tend to "erase" themselves in the absence of magnetic fields. Hence, to use such garnet films in any of the previous embodiments, it is only necessary to bias the film while the current in the sheet 26 is on, and it is not necessary to refresh the film. Because such films have no memory, no flaw image will be retained after the current in the sheet 26 is turned off.

Figure 8:
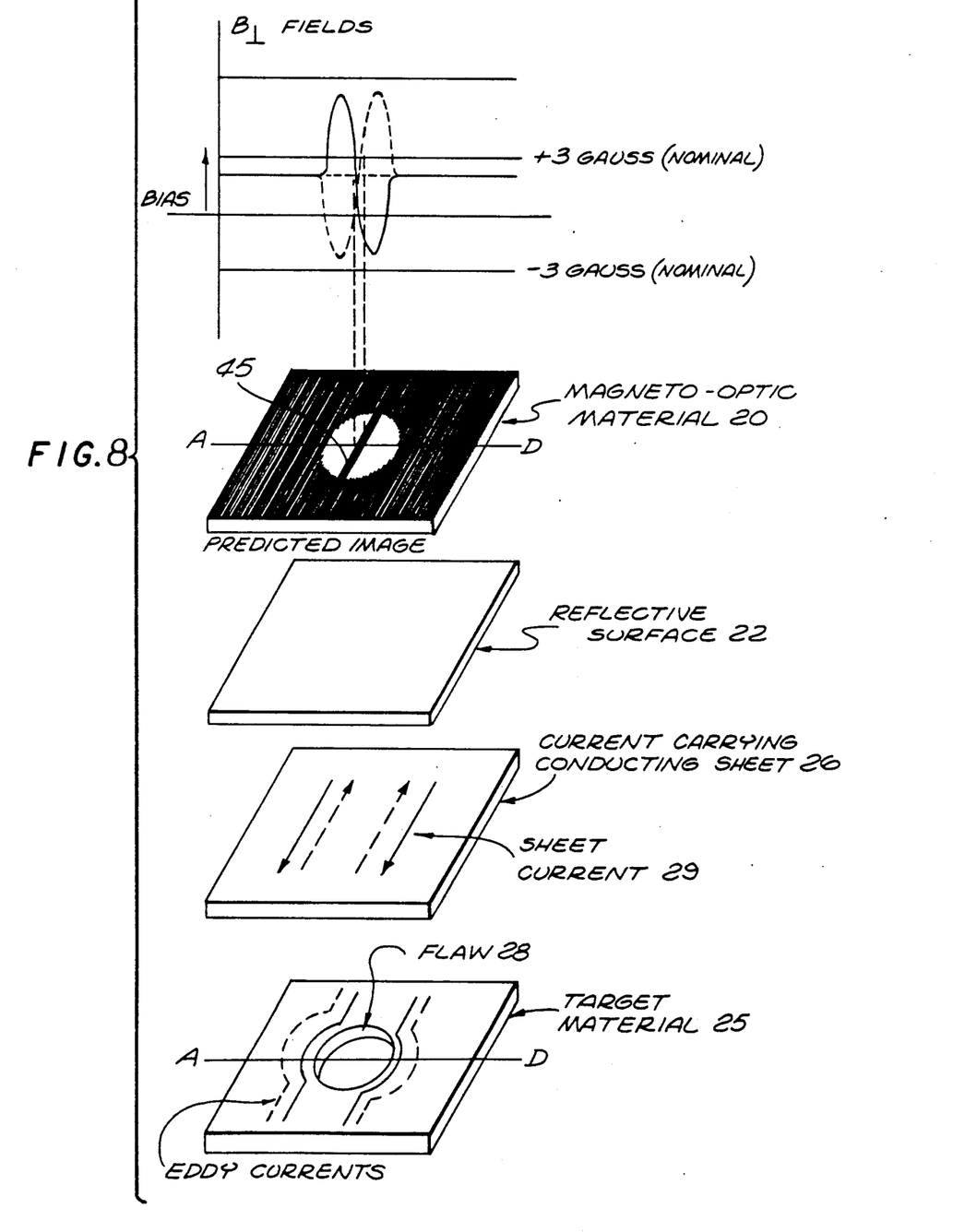
FIG. 8 illustrates how a flaw in an electrically conducting non ferromagnetic target material appears when viewed through the analyzer of the present invention.

Electric currents induced in 25 by currents in the conducting sheet 26, shown in FIG. 8, in a target material 25 containing a circular hole or flaw 28, or a rivet made of a material having an electrical conductivity generally different than the target material, illustrates how an image of the hole, or a flaw 28, is formed in a magneto-optic material 20 having a memory. Both the current in the coil 24, and the eddy currents passing close to the hole or rivet in the target material 25, produce magnetic fields which are perpendicular (B $\perp$ as shown in FIG. 8) to the magneto-optic material 20.

The bias magnetic field produced by the current in the coil 24 is also perpendicular to the magneto-optic material 20 and is generally slowly varying (approximately constant in time) with respect to the relatively high frequency eddy currents in the target material. In FIG. 8, the polarizing material 38 or 80 depending on the embodiment, and analyzer 44 are not shown. However, they are assumed to be set so that when the bias is "minus" 3 gauss or less (3 gauss is the magnitude of the collapse field of a typical magneto-optic material 20 of the type to be employed) the magneto-optic material 20 will look "black" or dark. As the bias increases from less than minus 3 gauss to less than "plus" 3 gauss as shown in FIG. 8, the combined fields (bias field plus the magnetic field from the eddy currents in the target material 25 flowing near the hole 28) exceed the collapse field of the magneto-optic material 20 and the magnetization in this material changes direction in a region which now appears to be "light" as seen through the analyzer 44.

Note the dark line 45 in FIG. 8 is a region of the magneto-optic material 20 which remains "black" as seen through 44 since the combined B fields (normal to the garnet film surface) do not exceed the collapse field of 20 in this region. Thus, the actual image as seen through 44 on 20 is a "light" circle with a "dark" line or bar down the middle. Had the analyzer 44 been originally set to make the background of 20 as seen through 44, light instead of dark, the result would have been a dark circle with bright bar down the middle. Note that in either case, these bars lie generally parallel to the direction of the sheet currents 29 in the current carrying sheet 26.

Flaws 28 in the target material with a geometry more complicated than a circular hole, produce more complicated distortions in the magnetic fields associated with the flow of eddy currents near the flaw. Nevertheless, if eddy current frequencies are sufficiently high (typically 10 to 100 kHz) these magnetic field distortions will be located close to the flaws, and consequently the images produced on 20 as seen through 44, will look very similar to the actual flaws in many cases of practical interest.

The bar down the middle of the hole image of FIG. 8 is an annoyance which can be eliminated by another embodiment. In this other embodiment, the current carrying sheet 26 is made to carry current in two orthogonal directions. These currents are also arranged to be in quadrature (90 degrees out of phase) with one another. These currents can be achieved in the current carrying sheet 26 by setting up corresponding orthogonal potential differences (in the current carrying sheet 26) which are also in quadrature. This is accomplished by the current generation means (quadrature current generator) 53 shown in FIG. 6. Of course, the quadrature current generator can be used in conjunction with any of the embodiments of the invention which are described herein. The net result of this arrangement is that the current in the current carrying sheet 26 will rotate in the plane of the sheet 26 at the dominant angular frequency of the applied currents in 26.

The resultant hole image will no longer have the bar down the middle as in FIG. 8. Instead, a hole (or a rivet) will look like a hole (or a rivet) but with a smaller circular area (analogous to the bar of FIG. 8) in its center.

This is a non-trivial improvement, because it means that flaw images will be similar to an average of images made with varying current directions. Since an image is generally difficult to form when the current direction lies parallel to the long axis of a flaw 28, this alternative embodiment insures that all cracks, no matter what their geometry or orientation relative to the orientation of the current in the carrying sheet 26, will be properly imaged.

Another method of maximizing the quality of the image produced by the present invention is to utilize a modulated light source. The light source, such as the external light source 30 shown in FIG. 2, is modulated in brightness in a sinusoidal or other similarly periodic fashion. The predominant frequency of oscillation of the light intensity is the same as that of the current in the coil 24 surrounding the stack. However, the phase of the light source intensity relative to the coil current phase is adjustable. The result is that one can have the light on maximum intensity when the best image (as partially determined by the level of current in coil 24) is present. In this way, the light is only on when a good image can be produced and not on when poor (low contrast) images would be produced. This not only saves energy (the light is on only when the image is good), but does not allow poor images to be averaged in with good ones, which would tend to "wash out" the image. Thus, the frequency of the light modulation (and the coil current frequency) can be well above that which the eye can detect. This means not only that the image quality (contrast) will be maximized when the light is on, but will not appear to flicker to the observer. Because the frequency of light modulation can be above that which the eye can detect, the light will appear to the eye and many cameras to be on all the time, in spite of the fact that the light source intensity is actually being modulated. In practice, a means for adjusting the phase of the light source modulation, relative to the current in the coil is provided. The phase is then adjusted until the maximum sharpness or brightness and contrast of the image is produced. This is shown schematically by the phase adjuster 51 in FIG. 1. It is to be understood that the phase adjustment means is not to be limited to the embodiment of FIG. 1, but can be used with any of the particular embodiments of the invention which are described herein.

It will be appreciated by those skilled in the art that the magneto-optic materials 20 and 21 described above may be replaced by an electro-optic material (including both solid and liquid electro-optic materials) and a means for supplying an appropriate bias electric field to the electro-optic material. Such an arrangement would be expected to produce images of flaws similar to the foregoing embodiments in which only magneto-optic materials were employed.

Accordingly, a method and apparatus for the direct visualization of surface and near surface cracks, flaws, etc. in non-ferromagnetic and ferromagnetic conducting materials has been disclosed. The invention provides a simple and economical means for detecting flaws not possible in the prior art involving conventional eddy current probe coils and the like. It will be understood that various changes may be made in the details, arrangements and proportions of the various elements of the present invention without departing from the spirit and scope of the invention. For example, it will also be apparent that the present invention has utility beyond the detection of flaws in non-organic materials and may be used to detect tumors or other discontinuities in biologic materials.

I claim:

1. A device for detecting a flaw, void, discontinuity and the like in a conducting target material, comprising:
   a layer of electrical insulator material disposed on top of said target material;
   a current carrying sheet disposed on top of said electrical insulator;
   a reflective surface disposed on top of said current carrying sheet;
   a magneto-optic material having a plurality of magnetic domains disposed on top of said reflective surface, said magneto-optic material comprising:
   a first magnetic epitaxial layer, said first magnetic epitaxial layer being optically transparent;
   a non-magnetic substrate layer disposed on top of said first magnetic epitaxial layer, said substrate layer being optically transparent;
   magnetic field generation means disposed about said magneto-optic material for generating and applying a variable magnetic field to said magneto-optic material;
   light generation means disposed near said magneto-optic material;
   a first polarizer disposed between said light generation means and said magneto-optic material;
   wherein said light generation means transmits a beam of light through said first polarizer and said magneto-optic material, said beam of light being reflected by said reflective surface back through said magneto-optic material, said magneto-optic material rotating a plane of polarization of said beam of light, the magnitude of said rotation being dependent on a realignment of said magnetic domains due to eddy currents in the target material, said beam of light then impinging on a second polarizer, said second polarizer passing said beam of light when said magnitude of said rotation is substantially equal to a predetermined value.

2. The device of claim 1, wherein said magnetic field generation means comprises a coil.

3. The device of claim 1, wherein said current carrying sheet is coupled to a current source, said current source generating electric currents in said current carrying sheet which in turn induce eddy currents in said target material, said eddy currents being distorted by flaws in said target material, and wherein said distortions in said eddy currents in turn cause distortions in a second magnetic field, said distortions in said second magnetic field being imaged by said magneto-optic material.

4. The device of claim 1, wherein the value of the angle of rotation of said plane of polarization of the incident light processing through said magneto-optic layer is denoted by the variable $\theta$ and is described by the following relationship:

$$\theta \alpha \theta f \overline{K} \cdot \overline{M}$$

where,
$\theta f =$ the specific Faraday rotation of said magneto-optic layer,
$\overline{K} =$ the wave vector of the incident polarized light,
$\overline{M} =$ the local magnetization of said magneto-optic layers.

5. The device of claim 1, wherein said magneto-optic material further comprises a second magnetic epitaxial layer disposed between said substrate and said first polarizer.

6. The device of claim 1, wherein electric current is injected into said target material by said current carrying sheet at a frequency sufficient to produce magnetic field variations at the surface of said target material and throughout said first magnetic epitaxial layer, said variations corresponding to flaws contained within said target material.

7. The device of claim 1, wherein said magnetic field generation means generates an alternating magnetic field, said alternating magnetic field varying at a first frequency, and wherein said incident polarized light is modulated at a second frequency, said second frequency being substantially equal to said first frequency.

8. The device of claim 7, wherein said apparatus further comprises a phase adjustment means for varying the phase of said modulated polarized light relative to the phase of said alternating magnetic field.

9. The device of claim 1 further comprising a current generation means for generating orthogonol currents in said current carrying sheet, said orthogonol currents being in quadrature with one another.

10. The device of claim 1, wherein said magnetic field generation means produces a bias magnetic field on said magneto-optic material for a period of time $t_o$, and then produces a refresh magnetic field on said magneto-optic material for a period of time $\Delta t$, where $t_o$ is substantially greater than $\Delta t$, said bias field sensitizing said magneto-optic material such that images of the magnetic fields associated with the eddy currents in the target material can be observed in said magneto-optic material, and said refresh field erasing said images.

11. The device of claim 10, wherein said bias and refresh magnetic fields have vector directions substantially 180° apart.

12. The device of claim 1 wherein said first magnetic epitaxial layer comprises a garnet film.

13. The device of claim 5 wherein said second magnetic epitaxial layer comprises a garnet film.

14. The device of claim 3 wherein said second magnetic field is varied at a rate within the range of 10 kHz to 100 kHz.

15. The device of claim 1 wherein said light generation means comprises an incandescent light bulb.

16. The device of claim 1 wherein said light generation means comprises a single-wavelength laser.

17. The device of claim 1 wherein said light generation means comprises an electro-luminescent panel.

18. The device of claim 1 wherein said variable magnetic field has a maximum value substantially equal to 3 gauss.

19. An apparatus for detecting a flaw, void, discontinuity and the like in a conducting target material, comprising:
a layer of electrical insulator material disposed on top of said target material;
a current carrying sheet disposed on top of said electrical insulator;
a light source disposed on top of said current carrying sheet;
a first polarizer disposed on top of said light source;
a magneto-optic material having a plurality of magnetic domains disposed on top of said first polarizer, said magneto-optic material comprising:
a first magnetic epitaxial layer, said first magnetic epitaxial layer being optically transparent;
a non-magnetic substrate layer disposed on top of said first magnetic epitaxial layer, said substrate layer being optically transparent;
magnetic field generation means disposed about said magneto-optic material for generating and applying a variable magnetic field to said magneto-optic material;
a second polarizer disposed a pre-determined distance away from said target material;
wherein said light source transmits a beam of light through said first polarizer and said magneto-optic material, said magneto-optic material rotating a plane of polarization of said beam of light, the magnitude of said rotation being dependent on a realignment of said magnetic domains due to eddy currents in the target material, said beam of light then impinging on said second polarizer, said second polarizer passing said beam of light when said magnitude of said rotation is substantially equal to a predetermined value.

20. The device of claim 19 wherein said magneto-optic material further comprises a second magnetic epitaxial layer disposed on top of said substrate.

21. The device of claim 19 wherein said first magnetic epitaxial layer comprises a garnet film.

22. The device of claim 19 wherein said second magnetic epitaxial layer comprises a garnet film.

23. The device of claim 19 wherein said second polarizer is disposed on top of said second magnetic epitaxial layer.

* * * * *